United States Patent [19]

Latter et al.

[11] Patent Number: 5,310,762
[45] Date of Patent: May 10, 1994

[54] MEDICAMENTS

[75] Inventors: Victoria S. Latter; Winston E. Gutteridge; Alan T. Hudson, all of Beckenham, England

[73] Assignee: Burroughs Wellcome Co., Research Triangle Park, N.C.

[21] Appl. No.: 796,324

[22] Filed: Nov. 22, 1991

Related U.S. Application Data

[62] Division of Ser. No. 394,224, Aug. 15, 1989, Pat. No. 5,206,268.

[30] Foreign Application Priority Data

Aug. 16, 1988 [GB] United Kingdom ............... 8819478
Aug. 16, 1988 [GB] United Kingdom ............... 8819479
Aug. 16, 1988 [GB] United Kingdom ............... 8819480

[51] Int. Cl.$^5$ ............................................. A61K 31/12
[52] U.S. Cl. ...................................................... 514/682
[58] Field of Search ........................................ 514/682

[56] References Cited

U.S. PATENT DOCUMENTS 4,981,874  1/1991  Latter et al. ............... 514/682
5,053,432  10/1991 Hudson et al. ............. 514/682

*Primary Examiner*—Jerome D. Goldberg
*Attorney, Agent, or Firm*—Donald Brown; Lawrence A. Nielsen; Hannah O. Green

[57] ABSTRACT

A method for treating or preventing a *Pneumocystis carinii* infection in a mammal by administering a certain naphthoquinone compound or physiologically acceptable salts thereof.

4 Claims, No Drawings

MEDICAMENTS

This is a divisional of copending application Ser. No. 07/394,224, filed on Aug. 15, 1989, now U.S. Pat. No. 5,206,268.

The present invention relates to the treatment and prophylaxis of *Pneumocystis carinii* infections. More particularly the invention is concerned with the use of naphthoquinones in the treatment and prophylaxis of *Pneumocystis carinii* infections, the use of said compounds for the manufacture of medicaments for the treatment and prophylaxis of *P. carinii* infections, and novel formulations containing said compounds.

*Pneumocystis carinii* is a parasite which has a natural habitat in lung tissue. In a host with a normal immune system *P. carinii* is not considered to be pathogenic. However, when the immune system is defective *P. carinii* is liable to cause pneumonia. There is a variety of circumstances in which the immune system may be defective or deficient. Thus, for example immune system deficiency is common in immature or premature infants (neonates). It may also result from suppression by certain drugs, which may be deliberate e.g. in certain patients receiving organ transplants, or unavoidable e.g. as a side-effect of cancer chemotherapy. Disordered growth of one or more constituent parts of the immune system, e.g. as in certain forms of cancer, may also result in immunodeficiency.

Immune deficiency may furthermore be caused by viral infections, including human immunodeficiency virus (HIV). It has been reported (Hughes, W. T. (1987) Treatment and Prophylaxis of *Pneumocystis carinii* pneumonia, Parasitology Today 3(11) 332–335) that at least 60% of patients with acquired immunodeficiency syndrome (AIDS) suffer from *Pneumocystis carinii* pneumonia.

In this specification the term "immunocompromised host" will be used to describe hosts with a deficient or defective immune system.

Without treatment, *Pneumocystis carinii* pneumonia is almost always fatal in immunocompromised hosts. The most widely used treatments for this condition are trimethoprim-sulphamethoxazole (cotrimoxaole) and pentamidine. However, both of these treatments have been reported to be only around 50–70% effective in AIDS patients and to produce a much higher than usual incidence of adverse reactions (about 50%) (Wofsy, C. B. Antimicrobial Agents Annual, 1986, Vol 1, p377–400). There is thus a need for new agents, especially for the prophylaxis of *P. carinii* pneumonia.

A wide range of naphthoquinones is known in the art. Such compounds have been variously described as having antimalarial, anticoccidial and antitheilerial activity. Some compounds have also been described as possessing activity against external parasites. Thus, Fieser et al, J. Amer. Chem. Soc. 1948, 70, 3156–3165 (and references cited therein) describes a large number of 2-substituted-3-hydroxy-1,4-naphthoquinones as having antimalarial activity. A number of these compounds have also been described in U.S. Pat. No. 2,553,648. Further classes of 2-substituted-3-hydroxy-1,4-naphthoquinones having activity as antimalarial, anticoccidial and/or antitheilerial agents are described in U.S. Pat. Nos. 3,367,830, and 3,347,742, U.K. Patent Specification No. 1553424, and European Patent Specifications Nos. 2 228, 77551 and 77550.

European Patent Application No. 123239 discloses synergistic combinations of anti-protozoal naphthoquinones and 4-pyridinols or alkanoic esters thereof, which are said to be especially useful for the treatment or prophylaxis of malaria.

European Patent No. 123,238 discloses 2-substituted-3-hydroxy-1,4-naphthoquinones of formula (I)

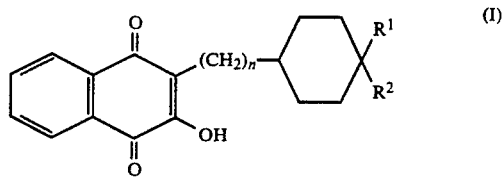

wherein either $R^1$ is hydrogen and $R^2$ is selected from $C_{1-6}$ alkoxy, aralkoxy, $C_{1-6}$ alkyl-$C_{1-6}$ alkoxy, phenyl substituted by one or two groups selected from halogen and $C_{1-6}$ alkyl, halogen and perhalo-$C_{1-6}$ alkyl or $R^1$ and $R^2$ are both $C_{1-6}$ alkyl or phenyl, and n is zero or 1, and physiologically acceptable salts thereof. Compounds of formula (I) wherein n is zero are said to be active against the human malaria parasite *Plasmodium falciparum* and also against Eimeria species such as *E. tenella* and *E. acervulina*, which are causitive organisms of coccidiosis. Compounds of formula (I) where n is 1 are said to be active against protozoa of the genus Theileria, in particular *T. annulata* and *T. parva*.

We have now found that a variety of naphthoquinones are active in vivo against *Pneumocystis carinii* pneumonia infections in rats.

In a first aspect the present invention provides a naphthoquinone for use in the treatment and/or prophylaxis of *Pneumocystis carinii* infections (e.g. *P. carinii* pneumonia) in mammals (including humans).

In another aspect the present invention provides the use of a naphthoquinone for the manufacture of a medicament for the treatment and/or prophylaxis of *Pneumocystis carinii* infections in mammals (including humans).

According to a further aspect the present invention provides a method of treating and/or preventing *Pneumocystis carinii* infections in a mammal which comprises administering to a mammal (including a human) suffering from or susceptible to infection with *P. carinii* pneumonia an effective amount of a naphthoquinone.

Prevention of *P. carinii* infections is particularly important in an immunocompromised host, as discussed hereinabove. In the case of immunosuppression resulting from HIV infection, prophylaxis may be required by those diagnosed as seropositive for HIV, and those with progressive generalised lymphadenopathy (PCL) or AIDS-related complex (ARC) as well as patients suffering from AIDS.

Naphthoquinones for use according to the present invention include 1,4-naphthoquinones of the general formula (II):

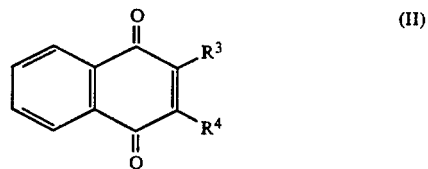

wherein $R^3$ is C1–35 non-aromatic hydrocarbon residue optionally substituted by one or more substituents selected from halo, $C_{1-6}$alkoxy, hydroxy, phenyl, phenyl-$C_{1-6}$alkoxy and phenyl-$C_{1-6}$alkyl, each such phenyl group or moiety being optionally substituted by one or more groups selected from C1-6 alkoxy, $C_{1-6}$ alkyl, C1-6alkoxy-$C_{1-6}$alkyl, hydroxy, halogen, halo-$C_{1-6}$alkyl, amino, and mono-or di-$C_{1-4}$alkyl-amino; and $R^4$ is hydroxy; halogen;
  a group $OCOR^5$, wherein $R^5$ is a $C_{1-10}$alkyl group, a $C_{3-10}$ cycloalkyl group, a $C_{1-10}$alkoxy group, or a phenyl or naphthyl group, each such $R^5$ group being optionally substituted e.g. by amino, mono-or di-$C_{1-4}$alkylamino, carboxy or hydroxy;
  a group $OR^6$ or $SR^6$, wherein $R^6$ is an optionally substituted $C_{1-10}$alkyl, $C_{3-10}$cycloalkyl, phenyl or naphthyl group as defined for $R^5$; or
  a group $NR^7R^8$, wherein $R^7$ and $R^8$ each independently represent hydrogen or $C_{1-4}$alkyl, or the group $NR^7R^8$ represents a 5–7 membered saturated heterocyclic ring, which may optionally contain a further heteroatom selected from nitrogen, oxygen or sulphur;
  with the proviso that when $R^4$ is hydroxy, $R^3$ is not a 4-(4-chlorophenyl)cyclohexyl group;
and physiologically acceptable salts and other physiologically functional derivatives thereof.

A $C_{1-35}$ non-aromatic hydrocarbon residue $R^3$ may be a straight or branched chain $C_{1-14}$ (e.g. $C_{1-8}$)alkyl or $C_{2-14}$ (e.g. $C_{2-8}$)alkenyl group or a $C_{3-10}$ (e.g. $C_{3-8}$)cycloalkyl group, each of which may optionally carry a $C_{3-10}$ (e.g. $C_{3-6}$)cycloalkyl group, and each of the aforesaid cycloalkyl groups optionally carrying a $C_{1-10}$ (e.g. $C_{1-4}$)alkyl group. The non-aromatic hydrocarbon residue $R^3$ preferably contains from 1 to 20 carbon atoms, e.g. 1 to 14 carbon atoms. Suitable residues $R^3$ include $C_{3-10}$cycloalkyl-$C_{1-8}$alkyl, $C_{1-10}$alkyl-$C_{3-10}$cycloalkyl, $C_{1-10}$alkyl-$C_{3-10}$cycloalkyl-$C_{1-10}$alkyl and $C_{3-10}$-cycloalkyl-$C_{3-10}$cycloalkyl.

Compounds of formula (II) containing an acidic hydroxy or carboxy group, such as compounds wherein $R^4$ is hydroxy, may form salts with bases, and compounds (II) containing a basic amino group may form salts with acids. Suitable base salts include inorganic base salts such as alkali metal (e.g. sodium and potassium) salts and alkaline earth metal (e.g. calcium) salts; organic base salts e.g. phenylethylbenzylamine, dibenzylethylenediamine, ethanolamine and diethanolamine salts; and amino acid salts e.g. lysine and arginine. Suitable acid addition salts include those formed from hydrochloric, hydrobromic, nitric, perchloric, sulphuric, citric, tartaric, phosphoric, lactic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic and glucuronic acids.

Without wishing to be bound by theory, it is believed that compounds of formula (II) wherein $R^4$ is a group—$OCOR^5$, $OR^6$, $SR^6$ or $NR^7R^8$ may act as pro-drugs or bioprecursors which are converted in vivo either by the host or the parasite to a compound of formula (II) wherein $R^4$ is hydroxy. Such compounds will be referred to hereinafter as "physiologically functional derivatives". Such compounds may also however possess intrinsic biological activity.

The invention includes within its scope the use of isomers of compounds of formula (II) and mixtures of such isomers. The compounds of formula (II) may exist in a tautomeric form in which the hydroxyl group donates its proton to one of the oxo groups and the use of such tautomeric forms is included within the scope of this invention. However, it is believed that the stable form is that shown in formula (II).

A preferred group of compounds for use according to the invention is that of formula (III):

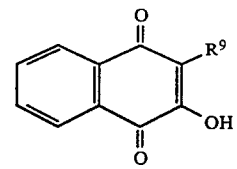
(III)

wherein $R^9$ is
  a $C_{1-10}$alkyl group;
  a $C_{5-7}$ cycloalkyl group (which may be optionally substituted by a straight or branched chain $C_{1-6}$ alkyl group, a halo-$C_{1-6}$alkyl group, a $C_{1-6}$alkoxy group or a phenyl group, the phenyl group itself being optionally substituted by one or more substituents selected from $C_{1-6}$ alkyl and halogen); or
  a $C_{1-10}$alkyl-$C_{5-7}$cycloalkyl group, wherein the cycloalkyl moiety may be optionally substituted as defined for the aforementioned $C_{5-7}$ cycloalkyl group; and
physiologically acceptable salts and other physiologically functional derivatives thereof.

Another group of compounds which may be used according to the present invention is that of formula (IV)

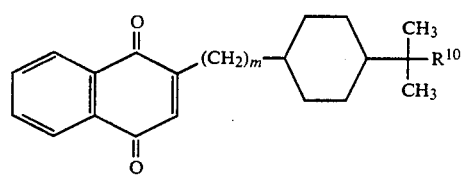
(IV)

wherein $R^{10}$ is an alkyl group of from 1 to 10 carbon atoms and m is 0 or 1, and physiologically acceptable salts and other physiologically functional derivatives thereof.

In the compounds of formula (IV) $R^{10}$ is suitably a straight-chain $C_{1-4}$ alkyl group, preferably methyl.

A further group of compounds which may be used according to the present invention is that of formula (I) as hereinbefore defined with the proviso that when n is zero, $R^2$ is not a chlorine atom, and physiologically acceptable salts and other physiologically functional derivatives thereof.

Further compounds within the scope of general formula (II) include those of formula (V)

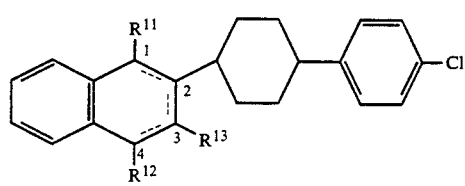
(V)

wherein $R^1$ and $R^1$ each represent =O and the dotted line represents a double bond between the 2 and 3 positions of the quinone ring, in which case $R^{13}$ represents a group —OCOR$^5$; a group OR$^6$ or SR$^6$; or a group NR$^7$R$^8$, wherein $R^5$, $R^6$, $R^7$ and $R^8$ are as hereinbefore defined; or the dotted line represents double bonds at the 1,2 and 3,4 positions of the quinol ring and $R^{11}$, $R^{12}$ and $R^{13}$ each represents a group —OCOR$^{14}$, wherein $R^{14}$ represents an optionally substituted $C_{1-10}$alkyl group.

Compounds of formula (V) are believed to be novel and form a further aspect of the present invention. As indicated above it is believed that such compounds may act as prodrugs or bio precursors of the corresponding compound wherein $R^{13}$ is hydroxy.

Compounds of formula (V) have been found to exhibit activity in vitro against the parasite *Plasmodium falciparum* and in vivo against the parasite *Plasmodium yoelii* as illustrated hereinafter. These compounds may therefore be useful in the treatment and/or prophylaxis of malaria.

A preferred compound of formula (V) is 2-acetoxy-3-[trans-4-(4-chlorophenyl) cyclohexyl]-1,4-naphthoquinone. This compound has the advantage of improved water-solubility as compared with the corresponding compound wherein $R^{13}$ is hydroxy.

A further preferred compound of formula (V) is 2-[trans-4-(4-chlorophenyl) cyclohexyl]-1,3,4-triacetoxynaphthalene. In contrast to the corresponding compound wherein $R^{13}$ is hydroxy, which is yellow, this compound is colourless, and may therefore have advantages in terms of its formulation and presentation.

Further derivatives which may be used in accordance with the present invention are those of formula (VI)

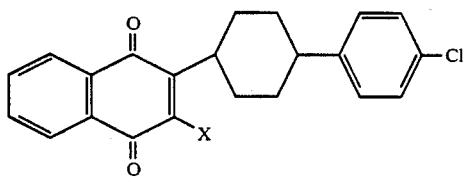

(VI)

wherein X is a halogen atom, e.g. a chlorine, bromine or iodine atom, preferably a chlorine atom.

The compound of formula (VI) wherein X is chlorine has previously been described as an intermediate e.g. in the preparation of the compound of formula (I) but no biological activity has been ascribed to it. In a further aspect therefore the present invention provides a compound of formula (VI) for use as a medicament, e.g. an antiprotozoal agent, or a medicament for the treatment of *Pneumocystis carinii* infections.

Particularly preferred compounds for use according to the present invention include:
2-(4-t-butylcyclohexyl)-3-hydroxy-1,4-naphthoquinone
2-(4-t-butylcyclohexylmethyl)-3-hydroxy-1,4-naphthoquinone
2-[4-(4-chlorophenyl)cyclohexyl]-3-chloro-1,4-naphthoquinone
and physiologically acceptable salts and physiologically functional derivatives thereof.

It will be appreciated that the compounds of formula (I) wherein $R^1$ is hydrogen, and the compounds of formulae (IV), (V) and (VI) may exist as the cis or trans isomer, that is to say that the cyclohexyl ring may be cis or trans substituted by the naphthoquinone nucleus and the substituent on the cyclohexyl ring. Both cis and trans isomers and mixtures thereof in any ratio may be used in accordance with the present invention. In general when the compound is in the form of a mixture of isomers the trans isomer will be present in an amount of about 50% or will be the predominant isomer but the use of mixtures in which the cis isomer predominates is also included within the scope of the invention. The specific ratio of isomers may be varied as required; typical mixtures include those in which the cis/trans isomer ratio is about 1:1, 40:60 and 5:98.

The synthesis of compounds of formulae (I) to (VI) may be effected by methods already known and described in the chemical literature (for example the patent specifications listed hereinbefore) or by analogous methods. In particular novel compounds of formula (V) may be prepared by the following methods which form a further aspect of this invention:

(a) reaction of a compound of formula (VI) wherein X is halogen or hydroxy, with a compound serving to introduce the required group $R^{13}$, and where appropriate the groups $R^{11}$ and $R^{12}$;

(b) reaction of a compound of formula (VII):

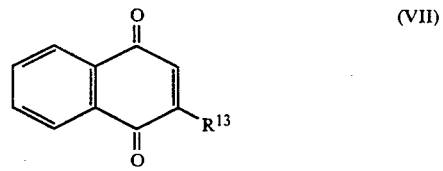

(VII)

wherein $R^{13}$ is as defined above with a donor compound serving to introduce the 4-(4-chlorophenyl)cyclohexyl group.

With regard to process (a) compounds (V) wherein $R^{11}$ and $R^{12}$ represent =O and $R^{13}$ represents a group OCOR$^5$ may be prepared by esterification of the compound (VI) wherein X is hydroxy. Esterification may be effected in conventional manner using the appropriate acid R$^5$COOH or acid derivative e.g. an acid anhydride, acid chloride or an activated ester such as an alkylhaloformate e.g. an alkylchloroformate. To prepare a compound of formula (V) wherein $R^{11}$, $R^{12}$ and $R^{13}$ each represent a group-OCOR$^{14}$, the esterification is carried out in the presence of a reducing agent, e.g. zinc.

Compounds of formula (V) wherein $R^{13}$ is a group OR$^6$ or SR$^6$ may be prepared from a compound (VI) wherein X is a halogen atom. Thus for example the group OR$^6$ may be introduced by reaction with the appropriate alcohol, e.g. methanol or ethanol in the presence of sodium, and the group SR$^6$ may be introduced by reaction with the corresponding thiol, R$^6$SH.

Compounds of formula (V) wherein $R^{13}$ is —NR$^7$R$^8$ may be prepared by reduction of the corresponding compound wherein $R^{13}$ is azido, e.g. using lithium aluminium hydride in tetrahydrofuran, followed where necessary and/or desired by alkylation of the resulting amino group. The azido compound may be prepared from a compound of formula (VI) wherein X is halogen, by reaction e.g. with sodium azide.

Compounds of formula (VI) may be prepared for example in an analogous manner to process (b) described below.

With regard to process (b), a suitable donor compound is the corresponding cycloalkane carboxylic acid which may undergo oxidative decarboxylation. For instance persulphate with a catalyst, such as silver ions, is convenient for the purpose, (c.f.Jacobson, N., et al., Annalen, 1972, 763, 135 and Acta Chem. Scand, 1973, 27, 3211). Conveniently ammonium persulphate can be used as the oxidising agent, and the catalyst is silver nitrate. Further details of this process are described in EPA 123238. The compound of formula (VII) used as starting material may be prepared from the corresponding 3-halo compound using methods analogous to process (a).

Hereinafter naphthoquinones active against *P. carinii*, including compounds more particularly described by formulae (I) to (V), and their physiologically acceptable salts and other physiologically functional derivatives will be referred to as the "naphthoquinone". It will be appreciated that the amount of the naphthoquinone required for use in the treatment or prophylaxis of *P. carinii* will depend inter alia on the activity of the particular compound, the route of administration, the age and weight of the mammal (e.g. human) to be treated and the severity of the condition being treated. In general, a suitable dose for administration to man for the treatment of P-carinii pneumonia is in the range of 0.1 mg to 200 mg per kilogram bodyweight per day, for example from 1 mg/kg to 100 mg/kg, particularly 10 to 50 mg/kg. For administration by inhalation the dose is conveniently in the range of 0.1 to 20 mg/kg/day, e.g. 0.5 to 10 mg/kg/day. It will be appreciated that for administration to neonates, lower doses may be required.

For prophylactic treatment the naphthoquinone may also be given less frequently, e.g. as a single dose on alternate days, once or twice per week or once or twice per month. The dosage for prophylactic treatment will depend Inter alia on the activity of the naphthoquinone, the frequency of administration, and, where a depot preparation or controlled release formulation is used the rate of release of the active ingredient. Thus for once-weekly administration a suitable prophylactic dose is in the range 0.05 to 100 mg/kg, e.g. 0.05 to 50 mg/kg particularly 5 to 50 mg/kg.

Suitable dosages of a compound of formula (V) for the treatment or prophylaxis of malaria in man are also within the ranges given above for the treatment and prophylaxis of *P. carinii* pneumonia.

For use according to the present invention the naphthoquinone is preferably presented as a pharmaceutical formulation.

Pharmaceutical formulations comprise the naphthoquinone or a physiologically acceptable salt or other physiologically functional derivative thereof together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

The naphthoquinone may conveniently be presented as a pharmaceutical formulation in unit dosage form. A convenient unit dose formulation contains the naphthoquinone in an amount of from 10 mg to 3 g e.g. 10 mg to 1 g.

Pharmaceutical formulations include those suitable for oral, topical(including dermal, buccal and sublingual),rectal or parenteral (including subcutaneous, intradermal, intramuscular and intravenous), nasal and intrapulmonary administration e.g. by inhalation. The formulation may, where appropriate, be conveniently presented in discrete dosage units and may be prepared by any of the methods well known in the art of pharmacy. All methods include the step of bringing into association the naphthoquinone with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the naphthoquinone. A tablet may be made by compression or moulding, optionally with one or more accessory ingredients. Compressed tablets may be prepared by compressing in a suitable machine the naphthoquinone in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the naphthoquinone, either alone or in admixture with one or more accessory ingredients, into the capsule shells and then sealing them in the usual manner. Cachets are analogous to capsules wherein the naphthoquinone together with any accessory ingredient(s) is sealed in a rice paper envelope. The naphthoquinone compound may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the naphthoquinone is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the naphthoquinone with the softened or melted carrier(s) followed by chilling and shaping in moulds.

Pharmaceutical formulations suitable for parenteral administration include sterile solutions or suspensions of the naphthoquinone in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the naphthoquinone may be in powder form which is constituted with a suitable vehicle, such as sterile, pyrogen-free water, before use.

The naphthoquinone may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing the naphthoquinone and desirably having a diameter in the range 0.5 to 7 microns are delivered into the bronchial tree of the recipient. Such formulations may be in the form of finely comminuted powders which may conveniently be presented in a pierceable capsule, for example of gelatin, for use in an inhalation device, or as a self-propelling formulation (also referred to as an aerosol formulation) comprising the naphthoquinone, a suitable liquid or gaseous propellant and optionally other ingredients such as a surfactant and/or a solid diluent. Suitable liquid propellants include propane and the chlorofluorocarbons, and suitable gaseous propellants include carbon dioxide. Suitable surfactants include sorbitan trioleate (which is available for example under the trade name "Arlacel 85"), Polysorbate 20 and oleic acid. Self-propelling formulations may also be employed wherein the active ingredient is dispensed in the form of droplets of solution or supension. The self-propelling formulation typically contains from 0.05 to 20 mg/ml e.g. 0.1 to 5 mg/ml of the active ingredient.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility the naphthoquinone may be in the form of a solution or suspension for use in an atomiser or nebuliser whereby an accelerated airstream or ultrasonic agitation is employed to produce a fine droplet mist for inhalation. Such solutions or suspensions may comprise, in addition to the naphthoquinone and solvent(s), optional ingredients such as surfactants. Suitable surfactants include those described above for self-propelling formulations. The solution or suspension typically contains from 0.05 to 20 mg/ml e.g. 0.1 to 5 mg/ml of the naphthoquinone. When a suspension of the naphthoquinone is employed, this compound is preferably in finely divided form, e.g. in micronised form.

Formulations suitable for nasal administration include presentations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the naphthoquinone in aqueous or oily solution or suspension.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

None of the references listed hereinabove contains an invitation to administer the compounds of formula (II) by the nasal or pulmonary route or any suggestion that the said compounds, if administered in such a manner, would be effective in the treatment of the conditions therein taught; the said disclosures likewise contain no description of any formulation suitable for administration by the nasal or pulmonary route.

Pharmaceutical formulations of the compounds of formula (II) adapted for administration by the nasal or pulmonary route are believed to represent novel formulations and thus form a further feature of the present invention.

Novel compounds of formula (V) may also be formulated in the manner described above for use in the treatment and/or prophylaxis of malaria and such formulations form a further aspect of the present invention.

The above naphthoquinones may also be used in accordance with the present invention in combination or concurrently with other therapeutic agents, for example agents used in the treatment of immunocompromised patients, including anticancer agents such as interferons e.g. alpha-interferons; antiviral agents such as azidothymidine (AZT,zidovudine), immunostimulants and immunodulators. The naphthoquinone may also be administered in combination with a 4-pyridinol compound, as described in EPA 123,239 e.g. 3,5-dichloro-2,6-dimethylpyridinol (meticlorpindol).

The following non-limiting examples illustrate inter alia the following aspects of the present invention:

the use of naphthoquinones in the treatment and prophylaxis of *P. carinii* infections;

novel pharmaceutical formulations;

novel compounds of formula (V).

EXAMPLE 1

2-[trans-4-(4-Chlorophenyl)cyclohexyl]-3-hydroxy-1,4-naphthoquinone a) 4-(4-Chlorophenyl)cyclohexane-l-carboxylic Acid

Acetyl chloride (30 g) and finely powdered aluminium chloride (60 g) were stirred together in carbon disulphide (120 ml) and then cooled to −50° C., in a $CO_2$/oxitol bath. Cyclohexene (30 g), previously cooled to −50° C., was added dropwise during 10 minutes while maintaining the temperature of the reaction mixture at below −20° C. The mixture was stirred at −50° C. for a further 60 minutes and the solvent then decanted to leave a gummy orange complex. A little chlorobenzene was added as the material warmed to ambient temperature; the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodium hydroxide and water, dried over anhydrous sodium sulphate and evaporated to dryness. The product was distilled in vacuo, the fraction boiling at 140°-154° C. (0.1 mm Hg) collected, diluted with an equal volume of petroleum ether (40-60), cooled to −60° C. and a continuous stream of nitrogen gas bubbled through, and the separated colourless solid recovered.

Bromine (2.8 ml) was added to a solution of sodium hydroxide (6.2 g) in water (42 ml) at 0° C. The above-obtained substituted hexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite was added to destroy excess hypobromite, the mixture cooled and then acidified to give a colourless solid. The solid was filtered off, washed with water, dried and recrystallised from ethanol to give 4-(4-chlorophenyl)cyclohexane-l-carboxylic acid, m.p. 254°–256° C.

b)

2-[4-(4-Chlorophenyl)cyclohexyl]-3-chloro-1.4-naphthoquinone

A mixture of 2-chloro-1,4-naphthoquinone (3.95 g, 0.02 mol), 4-(4-chlorophenyl)cyclohexane-l-carboxylic acid (4.9 g, 0.02 mol) and powdered silver nitrate (1.05 g, 0.0062 mol) was heated to reflux with vigorous stirring in 40 ml of acetonitrile. A solution of ammonium persulphate (12.0 g, 0.0525 mol) in 50 ml of water was added dropwise over 1 hour. The mixture was refluxed for 3 hours then cooled in ice for 30 mins, after which it was filtered, and the residual sticky solid extracted twice with boiling chloroform to remove inorganic material. The chloroform was removed by evaporation to leave a yellow-brown solid (ca 2.7 g). This was dissolved in 40 ml of boiling acetonitrile; a little insoluble material was removed by filtration. On cooling, the title compound separated as yellow crystals, (550 mg) m.p. 172°–175° C.

c)

2-[4-(4-Chlorophenyl)cyclohexyl]-3-hydroxy-1.4-naphthoquinone

The product of stage (b) was suspended in 10 ml of boiling methanol and 0.55 g of potassium hydroxide in 5.5 ml of water was added dropwise over 15 mins. The mixture was refluxed until a dark red solution formed, (after ca. 6 hrs) when 2 ml of concentrated hydrochloric acid was cautiously added dropwise. The mixture was cooled and filtered, and the solid residue washed thoroughly with water. The water washings were re-acidified and filtered. The combined solid residues (500 mg) mp 200°–209°, were recrystallised from acetonitrile to give the title product as the trans-isomer (300 mg) m.p. 216°–219° C.

EXAMPLE 2

2-Methoxy-3-[trans-4-(4-chlorophenyl)cyclohexyl]-1,4-naphthoquinone

Sodium (0.3 g, 0.013mol) was dissolved in 20 ml of methanol and the compound of Example l(b) (1.5 g, 0.004mol) was added. The mixture was warmed to reflux for 4 hours, then evaporated under reduced pressure. The dark red solid which remained was partitioned between water and chloroform. The chloroform layer was washed with ice cold dilute sodium hydroxide, followed by water and was then dried and evaporated to give a yellow solid (900 mg). This was recrystallised from acetonitrile to give the impure product (800 mg) mp 117°–120°, which was further recrystallised from ethanol to give the title compound (600 mg) mp 120°–122°.

EXAMPLE 3

2-Amino-3-[trans-4-(4-chlorophenyl)cyclohexyl]-1,4-naphthoquinone a)

2-Azido-3-[trans-4-(4-chlorophenyl)cyclohexyl]-1,4-naphthoquinone

A solution of sodium azide (0.42 g, 0.006mol) in 6 ml of water was added to a suspension of the compound of Example 1(b) (1.1 g, 0.003mol) in 15 ml of ethanol. The mixture was heated to reflux with stirring and then a further 15 ml of ethanol and 6 ml of water were added. Heating under reflux was continued for 4 hours followed by cooling in a refrigerator for 1 hour. The resulting yellow crystals were filtered off and washed with water and ethanol to give the impure title compound (0.9 g) mp 130°–135°. This material was used in the next stage without further purification.

b)

2-Amino-3-[trans-4-(4-chlorophenyl)cyclohexyl]-1,4-naphthoquinone

The impure product of stage (a) (0.9 g) was dissolved in dry tetrahydrofuran (THF) and added dropwise to a suspension of lithium aluminium hydride (2.0 g) in THF. The mixture was stirred at room temperature for 1 hour and then 2.0 ml of water was added dropwise with caution. A current of air was passed through the mixture for 1 hour and then 0.7 g of sodium hydroxide in 6 ml of water was added. The mixture was filtered and washed with THF. The filtrate was evaporated to dryness leaving an amorphous orange material which was triturated with SVM whereupon orange crystals formed. These were filtered off, washed well with SVM and dried to yield a first crop of product (200 mg) mp 210°–215°. The reaction was repeated to give a further crop of product (300 mg) mp 200°–210°. The two crops were combined and chromatographed, eluting with chloroform, to give the title compound (350 mg) mp 212°–215°.

EXAMPLE 4

2-[trans-4-(4-Chlorophenyl)cyclohexyl]-3-(3-dimethylaminopropoxy)-1,4-naphthoquinone Hydrochloride Sodium (0.10 g, 4.5 mmol) was dissolved in 3-dimethylamino-propan-1-ol (1.55 g, 5 eq) and cooled and the compound of Example 1(b) (1.15 g, 3 mmol) was added. The mixture was stirred at room temperature for 1 hour, following which acetic acid (1 ml) was added and the mixture diluted with toluene (30 ml). The solution was washed with water (4×20 ml) dried (MgSO4) and evaporated in vacuo to a purple semi solid. This was taken up in acetone and a mixture of diethyl ether and hydrochloric acid added until the purple solution turned orange. The solution was evaporated in vacuo to dryness and washed several times with toluene to give a yellow,/beige solid, which was recrystallised from methanol/toluene (1:99) to give the title compound as a yellow/green crystalline solid (0.92 g) mp 191°–194°.

EXAMPLE 5

2-Acetoxy-3-[trans-4-(4-chlorophenyl)cyclohexyl]-1,4-naphthoquinone

The compound of Example 1(c) (1.5 g, 0.004mol) was suspended in acetic anhydride (3 ml) and a few drops of concentrated sulphuric acid were added with vigorous stirring. A further quantity of acetic anhydride (3 ml) was then added, the mixture stirred for 30 minutes and then poured into 15 ml of water causing a vigorous reaction. The resulting mixture was cooled in ice and filtered to give pale yellow crystals which were washed with water and dried to give the impure product (1.6 g) mp 149°–152°. This was recrystallised from 100 ml of SVM to give the title compound (1.3 g) mp 158°–160°.

EXAMPLE 6

2-Ethoxycarbonyloxy-3-[trans-4-(4-chlorophenyl)cyclohexyl]-1,4 Naphthoquinone

The compound of Example 1(c) (1.1 g, 0.003mol) and pyridine (0.24 g, 0.003mol) was stirred in 5 ml of toluene and cooled in a water bath while 4 ml of ethyl chloroformate was added dropwise over a period of 15 minutes. The mixture was stirred for a further 30 minutes then poured into a mixture of ethyl acetate and water. The organic layer was separated, dried and evaporated to a yellow solid which was recrystallised from chloroform/petrol to give the impure product (850 mg) mp 145°–149°. This material was dissolved in chloroform, washed several times with ice cold 0.1N sodium hydroxide and then water. The organic layer was dried and evaporated to give product (450 mg) mp 147°–9°. The reaction was repeated on the same scale, the product combined with the aforementioned material and then recrystallised from chloroform/petrol to give the title compound (1.3 g) mp 153°–155°.

EXAMPLE 7 b

2-[trans-4-(4-Chlorophenyl)cyclohexyl]-3-(4-dimethylaminobenzoyloxy)-1,4-naphthoquinone The compound of Example 1(c) (2.0 g, 5.4 mmol) in dry toluene (50 ml) containing dry pyridine (0.44 g, 1 eq) was stirred at around room temperature. 4-Dimethylaminobenzoyl chloride (1 g, 1 eq) in dry toluene (25 ml) was added dropwise over 15 minutes. The mixture was stirred at around room temperature for 1 hour, heated at reflux for 10 hours, left standing for 38 hours, and then refluxed for a further 7 hours. The mixture was then cooled, washed with water, sodium bicarbonate solution and again with water, dried (MgSO$_4$) and evaporated in vacuo to a yellow solid which was recrystallised from ethanol to give the title compound (1.25 g) mp 117°–121° (shrinks above 113°).

EXAMPLE 8

2-[trans-4-(4-Chlorophenyl)cyclohexyl]-1,3,4-triacetoxynaphthalene

The compound of Example 1(c) (1.0 g) and zinc dust (1.0 g) was stirred at room temperature for 24 hours in acetic anhydride (6 ml) with one drop TEA. The reaction mixture was filtered and added to water (50 ml) and stirred for one hour. The resulting white precipitate was filtered, washed with water (4×20 ml) and dried to give the title compound (0.4 g) mp 177°–179°.

EXAMPLE 9

The following examples illustrate conventional pharmaceutical formulations containing as active ingredient the compound 2-(4-t-butylcyclohexyl)-3-hydroxy-1,4-naphthoquinone (Compound B) which may be employed in accordance with the present invention:

A. Injectable Solution

A solution for intramuscular injection may be prepared by mixing:

| | |
|---|---|
| Compound B | 9.5 parts by weight |
| Dimethyl sulphoxide | 19.0 parts by weight |
| Sorbitan monooleate | 4.5 parts by weight |
| Corn oil | 67.0 parts by weight |
| | 100.0 |

B. Injectable Solution

| | |
|---|---|
| Compound B | 5 parts by weight |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

C. Tablet

| | |
|---|---|
| Compound B | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

D. Oral Suspension

| | |
|---|---|
| Compound B | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

E. Injectable Suspension

| | |
|---|---|
| Compound B | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

F. Capsule

| | |
|---|---|
| Compound B | 100 mg |
| Starch 1500 | 150 mg |
| Magnesium stearate filled into a hard gelatin capsule | 2.5 mg |

EXAMPLE 10

The following examples illustrate novel pharmaceutical formulations according to the present invention.

15

A. Suspensions for Nebulisation

| a) Compound B, sterile | 1.0 mg |
|---|---|
| Water for Injections | to 10.0 ml |

Disperse the naphthoquinone in the Water for Injections previously sterilised in a sterile container. Fill in to sterile glass ampoules, 10 ml/ampoule under aseptic conditions, and seal each ampoule by fusion of the glass.

| b) Compound B, micronised | 1.0 g |
|---|---|
| Polysorbate 20 | 0.1% w/v |
| Water for Injections | to 10 ml |

Disperse the Polysorbate 20 in the Water for Injections, followed by Compound B. Fill into sterile glass ampoules, 10 ml/ampoule under aspetic conditions, and seal the ampoules by fusion of the glass.

B. Aerosol Formulations

| a) Compound of Example 1, micronised | 1.0 mg |
|---|---|
| Aerosol propellant | to 5.0 ml |

Suspend the micronised naphthoquinone in the aerosol propellant. Fill this suspension into preformed aerosol cannisters, 5 ml/cannister under pressure, through the valve orifice.

| b) Compound B, micronised | 1.0 mg |
|---|---|
| Arlacel 85 | 0.1% w/v |
| Aerosol propellant | to 5 ml |

Disperse the Arlacel 85 in the aerosol propellant and then add compound B. Fill the suspension into preformed aerosol cannisters, 5 ml/cannister under pressure, through the valve orifice.

C. Powder Inhalation

| Compound B, micronised | 1.0 mg |
|---|---|
| Lactose | 29.0 mg |

Triturate and blend the micronised naphthoquinone with the lactose. Fill the resulting powder blend into hard gelatin capsule shells, 30 mg per capsule.

D. Nasal Drops

| Compound B | 100.0 mg |
|---|---|
| Methylhydroxybenzoate | 10.0 mg |
| Water for Injections | to 10.0 ml |

Disperse the naphthoquinone and the methylhydroxybenzoate in the Water for Injections. Fill this suspension into suitable dropper bottles, 10 ml/bottle, and close by securing the dropper nozzle and bottle cap.

16

BIOLOGICAL TEST RESULTS

EXAMPLE 11

Activity against *Pneumocystis carinii*

Test Compounds

A: 2-[4-(4-chlorophenyl)cyclohexyl]-3-chloro-1,4-naphthoquinone

B: 2-(4-t-butylcyclohexyl)-3-hydroxy-1,4-naphthoquinone

C: 2-(4-t-butylcyclohexylmethyl)-3-hydroxy-1,4-naphthoquinone a) Treatment

Groups of 10 rats were treated with dexamethasone to allow latent *Pneumocystis carinii* infection to develop. Tetracycline was also administered to protect against bacterial infections. Test compounds (A)–(C) were administered orally by stomach tube from the beginning of week 5 to the end of week 7, at doses of 50, 75 and 100 mg/kg/day. In parallel with each test compound, Celacol was administered to one group of rats (also treated with dexamethasone and tetracycline) as a control.

At the end of the test period the animals were sacrificed and autopsies carried out. The lungs were removed and the right lung bisected. An imprint was made onto microscope slides and stained with toluidine blue. One half of the lung was placed in formalin, processed in paraffin blocks, sectioned and stained by the Gomori methanamine silver nitrate method.

After autopsy the extent of *P. carinii* pneumonitis was scored under coded study as none if no organism seen; 1+ if *P. carinii* cysts seen sparsely distributed with less than one per 25 high power field (h.p.f.); 2+ if focal areas of *P. carinii* pneumonitis surrounded by 10 to 25 h.p.f. of normal lung and 3+ if lung diffusely and extensively involved with organisms in almost all h.p.f.s.

The results are given in Table 1 below.

TABLE 1

| Test Compound | GROUP (Dose/ kg/day) | SCORE | | | | | NO. INFECTED/ NO. EXAMINED | % INFECTED |
|---|---|---|---|---|---|---|---|---|
| | | 0 | 1 | 2 | 3 | 4 | | |
| A | Celacol | 0 | 8 | 7 | 0 | 0 | 15/15 | 100 |
| | 25 mg/kg | 0 | 5 | 6 | 3 | 0 | 14/14 | 100 |
| | 50 mg/kg | 0 | 8 | 5 | 2 | 0 | 15/15 | 100 |
| | 100 mg/kg | 4 | 6 | 4 | 1 | 0 | 11/15 | 73 |
| B | Celacol | 0 | 8 | 2 | 3 | 2 | 15/15 | 100 |
| | 25 mg/kg | 0 | 7 | 7 | 1 | 0 | 15/15 | 100 |
| | 50 mg/kg | 1 | 8 | 4 | 1 | 0 | 13/14 | 93 |
| | 100 mg/kg | 3 | 8 | 3 | 0 | 1 | 12/15 | 80 |
| C | Celacol | 0 | 8 | 2 | 3 | 2 | 15/15 | 100 |
| | 25 mg/kg | 1 | 3 | 2 | 4 | 4 | 13/14 | 93 |
| | 50 mg/kg | 0 | 2 | 6 | 4 | 2 | 14/14 | 100 |
| | 100 mg/kg | 1 | 4 | 2 | 6 | 0 | 12/13 | 92 |

EXAMPLE 12

Antimalarial Activity of Compounds (V)

Test Methods

Activity against *Plasmodium falciparum* In Vitro

The test method was modification of that described by Desjardins et al. Antimicrob. Agents and Chemotherapy, 1979, 16, 710–718. Compounds were dissolved in ethanol at a concentration of $4.8 \times 10^{-3}$M and dilutions down to $1 \times 10^{-4}$M were made. The drug solutions were serially diluted using RPMI 1640 medium + 10% human plasma in microtitration plates.

Parasitised and fresh red blood cells were added, together with G-$^3$H-hypoxanthine, in RPMI 1640 medium + 10% human plasma and the cultures incubated for 48 hours. Cultures were then harvested, the particulate contents collected on a glass fibre filter paper and washed copiously with water. The filter papers were dried and the radioactivity measured using a scintillation counter. Infected untreated and uninfected untreated cultures were included as controls.

The results are shown in Table 2.

Activity against *Plasmodium yoelii* In Vivo

The naphthoquinone was suspended in 0.25% (w/v) celacol in water by milling for 16-24 hours at 26° C. The suspensions were subsequently serially diluted with 0.25% (w/v) celacol in water.

At time 0, 0.1 ml of a suspension of $5 \times 10^6$ *P. yoelii*-parasitised red blood cells/ml of phosphate saline were injected intravenously into 15-20 g mice through a tail vein. Groups of 5 mice per treatment were dosed orally at times 6, 22, 30, 46, 54, 70 and 78 hours with 0.2 ml of the drug suspension. The compound of Example 4 was also administered intravenously. Tail-blood smears were taken at 96 hours, stained with Giemsa and the percentage of red blood cells infected determined and compared to untreated, infected controls. Percent inhibition was correllated with dose to provide ED$_{50}$ values. The results are shown in Table 2 below.

TABLE 2

| | Antimalarial activity in vitro and in vivo | | |
|---|---|---|---|
| | | In vivo | |
| Compound of Example No: | In vitro IC$_{50}$(μM) | ED$_{50}$ oral | mg/kg. i.v. |
| 1C | 0.002 | 0.03 | |
| 2 | 0.36 | 5.8 | |
| 3 | 1.14 | 1.26 | |
| 4 | 0.059 | 0.61 | 2.08 |
| | | 0.68 | |
| 5 | 0.068 | 0.12 | |
| 6 | 0.080 | 0.09 | |
| 7 | 0.22 | 0.12 | |

We claim:

1. A method of treating in a mammal *Pneumocystis carinii* infections which comprises administering to said mammal suffering with *P. carinii* an effective treatment amount of a naphthoquinone of the general formula:

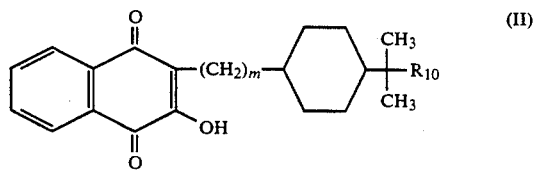

wherein R$^{10}$ is an alkyl group of from 1 to 10 carbon atoms and m is 0 to 1; and physiologically acceptable salts thereof.

2. A method according to claim 1 wherein the naphthoquinone is 2-(4-t-butylcyclohexyl)-3-hydroxy-1,4-naphthoquinone.

3. A method according to any one of claims 1 or 2 wherein the compound of formula is administered in an amount of from 10 to 50 mg per kilogram of mammal body weight per day.

4. A method according to claim 2 or 3 wherein the mammal is a human.

* * * * *